US011501860B2

(12) United States Patent
Arai

(10) Patent No.: US 11,501,860 B2
(45) Date of Patent: *Nov. 15, 2022

(54) MEDICAL INFORMATION TERMINAL

(71) Applicant: CANON KABUSHIKI KAISHA, Tokyo (JP)

(72) Inventor: Hiroshi Arai, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 129 days.

This patent is subject to a terminal disclaimer.

(21) Appl. No.: 16/511,986

(22) Filed: Jul. 15, 2019

(65) Prior Publication Data

US 2019/0341131 A1    Nov. 7, 2019

Related U.S. Application Data

(63) Continuation of application No. 14/138,952, filed on Dec. 23, 2013, now Pat. No. 10,395,763.

(30) Foreign Application Priority Data

Dec. 28, 2012    (JP) .................................. 2012-288607

(51) Int. Cl.
    *G16H 10/60*    (2018.01)

(52) U.S. Cl.
    CPC .................................. *G16H 10/60* (2018.01)

(58) Field of Classification Search
    CPC ................ G16H 10/60; G06F 21/6245; G06F 2221/2111; H04L 63/107; H04L 67/18; H04W 4/02

(Continued)

(56) References Cited

U.S. PATENT DOCUMENTS

2007/0006316 A1\* 1/2007 Veselova ............. G06F 21/6245
                                                           726/26
2008/0241806 A1\* 10/2008 Nomura ................. G09B 23/28
                                                           434/262

(Continued)

FOREIGN PATENT DOCUMENTS

JP    2006-202130 A    8/2006
JP    2008-250550 A    10/2008

(Continued)

OTHER PUBLICATIONS

Erickson et al., "Caring for Patients While Respecting Their Privacy: Renewing Our Commitment", May 31, 2005, OJIN: The Online Journal of Issues in Nursing. vol. 10 No. 2, Manuscript 1, DOI: 10.3912/OJIN.Vol10No02Man01 (Year: 2005).\*

(Continued)

*Primary Examiner* — Joy Chng
(74) *Attorney, Agent, or Firm* — Venable LLP

(57) ABSTRACT

A medical information terminal for input and display of medical information of a patient comprises a position information obtaining unit that obtains position information of the medical information terminal, an information concealing level setting unit that sets an information concealing level for description contents of each item of the medical information, and an information concealing unit that determines an information display threshold value indicating a threshold value at which the description contents of each item are displayed according to the position information obtained by the position information obtaining unit and conceals the description contents of each item if the information concealing level of each item of the medical information is at the information display threshold value or more.

22 Claims, 13 Drawing Sheets

(58) Field of Classification Search
USPC .......................................................... 705/2–3
See application file for complete search history.

(56) References Cited

U.S. PATENT DOCUMENTS

| 2011/0191862 A1* | 8/2011 | Mandava | H04L 63/107 |
| | | | 726/28 |
| 2011/0298817 A1* | 12/2011 | Oshinome | G06F 21/84 |
| | | | 345/589 |
| 2014/0075493 A1* | 3/2014 | Krishnan | H04L 67/52 |
| | | | 726/1 |

FOREIGN PATENT DOCUMENTS

| JP | 2009-122912 A | 6/2009 |
| JP | 2009-288856 A | 12/2009 |
| JP | 2011-136054 A | 7/2011 |

OTHER PUBLICATIONS

Japanese office action in counterpart application No. 2012-288607 dated Mar. 28, 2017 (9 pages including translation).

* cited by examiner

FIG. 4

| ITEM NAME | INFORMATION CONCEALING LEVEL |
|---|---|
| NAME | 80 |
| ADDRESS | 80 |
| TELEPHONE NUMBER | 80 |
| DATE OF BIRTH | 80 |
| DISEASE NAME | 70 |
| MEDICINE NAME | 70 |
| DIAGNOSIS IMAGE | 50 |

FIG. 6

| POSITION ID | GPS INFORMATION | INFORMATION DISPLAY THRESHOLD VALUE |
|---|---|---|
| 1 | (35.5308641, 139.6970844) | 100 |
| 2 | (35.5665172, 139.6822241) | 100 |
| 3 | (35.538933, 139.680422) | 100 |
| DEFAULT | ..... | 75 |

FIG. 11

| POSITION ID | PATIENT CLINICAL RECORD ID | GPS INFORMATION | INFORMATION DISPLAY THRESHOLD VALUE |
|---|---|---|---|
| 1 | 401, 402 | (35.5308641, 139.6970844) | 100 |
| 2 | 401 | (35.5665172, 139.6822241) | 100 |
| 3 | 402 | (35.538933, 139.680422) | 100 |
| DEFAULT | ⋯⋯ | ⋯⋯ | 75 |

FIG. 12

| ITEM NAME | TARGET DESIGNATION | INFORMATION CONCEALING LEVEL |
|---|---|---|
| NAME | — | 80 |
| ADDRESS | — | 80 |
| TELEPHONE NUMBER | — | 80 |
| DATE OF BIRTH | — | 80 |
| DISEASE NAME | — | 70 |
| MEDICINE NAME | — | 70 |
| DIAGNOSIS IMAGE | — | 50 |
| DIAGNOSIS IMAGE | IMAGE 501 | 80 |

FIG. 14

| ITEM NAME | TARGET DESIGNATION | INFORMATION CONCEALING LEVEL |
|---|---|---|
| NAME | — | 80 |
| ADDRESS | — | 80 |
| TELEPHONE NUMBER | — | 80 |
| DATE OF BIRTH | — | 80 |
| DISEASE NAME | — | 70 |
| DISEASE NAME | NEUROPSYCHIATRIC DISEASE | 80 |
| MEDICINE NAME | — | 70 |
| DIAGNOSIS IMAGE | — | 50 |
| FINDING | — | 50 |
| FINDING | NEUROPSYCHIATRIC DISEASE | 80 |

MEDICAL INFORMATION TERMINAL

CROSS-REFERENCE TO RELATED APPLICATIONS

This application is a continuation of U.S. patent application Ser. No. 14/138,952, filed on Dec. 23, 2013, which claims the benefit of priority from Japanese Application No. 2012-288607 filed Dec. 28, 2012. The contents of the aforementioned applications are incorporated herein by reference in their entireties.

BACKGROUND OF THE INVENTION

Field of the Invention

The present invention relates to a medical information terminal. Particularly, the present invention relates to a portable medical information terminal used for an electronic clinical record card, an image control system and the like relating to a medical information input act.

Description of the Related Art

On a medical treatment site such as a hospital, paper clinical record cards in a predetermined format have been used for recording a condition or a treatment process of a patient. However, problems of storage places, a burden of manual copying work, difficulty of search and the like are pointed out for the paper clinical record card, which contains medical information. Thus, digitalization of the paper clinical record card has progressed.

On the medical treatment site, a house visit is made, that is, a doctor directly visits the house of a patient for practicing medicine for a patient who has difficulty in going to hospital. In a hospital introduced an electronic clinical record card system, a doctor stores an electronic clinical record card of a patient for the house visit in a medical information terminal and carries the medical information terminal with him/her.

Since patients' clinical record cards contain highly personal information such as names of diseases, utmost care is required in handling of the electronic clinical record card to be taken out. On the other hand, it is expected that, if a doctor can browse some patient information by using the medical information terminal while the doctor is making a visit, medical examination of the patient can be smoothly conducted. However, in the case of browsing of the patient's clinical record during a visit, there is a concern that a third party other than the doctor and the patient might peep the clinical record information, and highly personal information might leak. If the doctor loses the medical information terminal storing the patent clinical record during the visit, it is also likely that the patient information leaks.

Thus, a method of preventing inadvertent leakage of medical information to a third party by setting data to be copied to the medical information terminal from a system in the hospital in advance is proposed (see Japanese Patent Application Laid-open No. 2011-136054).

Moreover, from the viewpoint of protection of secret, a method of executing a peeping prevention function according to a position is proposed in the case of a mobile phone (see Japanese Patent Application Laid-open No. 2009-288856). In this method, the peeping prevention function limiting display is executed at positions other than the position registered in the mobile phone. Specifically, an extraction condition for specifying a target of the peeping prevention function is set in advance in the mobile phone, and when the mobile phone is not at the position set in advance, the peeping prevention function is executed for a portion matching the extraction condition.

Other than the above, from the viewpoint of protecting personal information of patients, a method of limiting display in a medical examination assisting apparatus is proposed (see Japanese Patent Application Laid-open No. 2008-250550). In this method, information of the patient currently subjected to a house visit is displayed on an examination list display portion of the medical examination assisting apparatus, while information not directly required for the examination such as the names, addresses and the like of other patients is not displayed. As a result, the doctor or a clinical technologist can grasp a progress situation of the examination as a whole while personal information of other patients can be protected, since the names of the patients other than the patient subjected to the house visit cannot be discriminated even if a screen of the examination assisting apparatus is seen by the patient during medical examination.

SUMMARY OF THE INVENTION

However, with the configuration described in Japanese Patent Application Laid-open No. 2011-136054, secrecy is improved by setting data not to be taken out of a hospital, but diagnosing efficiency of a doctor might deteriorate if an amount of data that cannot be taken out increases. Moreover, from the viewpoint of prevention of mistaking a patient for another patient, information such as names, addresses and the like of patients is data that should be taken out. Thus, if the information is peeped or a terminal is lost, personal information protection is not sufficient.

Moreover, with the configuration described in Japanese Patent Application Laid-open No. 2009-288856, the peeping prevention function works when the mobile phone is present at a position other than the positions specified by a user of the mobile phone in advance. A portion matching the condition set by the user is equally made difficult to be seen. That is, the items matching the condition become difficult to be seen since the peeping prevention function works for them. Thus, in order to browse some items basically but to prevent only specific description contents in the information from being peeped in an operation of the electronic clinical record cards, fine conditions should be set. Moreover, since peeping prevention function works uniformly, it is difficult not to display the same descriptions in a certain item but to display them in the other items.

With the configuration described in Japanese Patent Application Laid-open No. 2008-250550, patient information other than the target patient is concealed by selecting a patient to be subjected to examination. Since a target is an electronic clinical record display device in an examination room, personal information of the other patients can be protected. However, if the terminal is to be taken out of a hospital, information can be browsed by selecting the patient, and thus, personal information protection is not sufficient against peeping by a third party or loss of a terminal.

The present invention has been made in view of the above circumstances, and automatically conceals information in a medical information terminal, which is set in advance in patient electronic medical record information and might lead to personal identification, according to the position by specifying a use position of the medical information terminal.

In order to solve the problems discussed above, the present invention provides a medical information terminal for input and display of medical information of a patient, comprising a position information obtaining unit that obtains position information of the medical information terminal, an information concealing level setting unit that sets an information concealing level for description contents of each item of the medical information, and an information concealing unit that determines an information display threshold value indicating a threshold value at which the description contents of each item are displayed according to the position information obtained by the position information obtaining unit and conceals the description contents of each item if the information concealing level of each item of the medical information is at the information display threshold value or more.

According to the present invention, medical information of a patient can be concealed according to the position of the medical information terminal and can reduce a concern of leakage of personal information through peeping by a third party other than a doctor and the patient.

Further features of the present invention will become apparent from the following description of exemplary embodiments with reference to the attached drawings.

BRIEF DESCRIPTION OF THE DRAWINGS

FIG. 4 is a table illustrating an example of the information concealing level table generated by the processing for generating the information concealing level table.

FIG. 6 is a table illustrating an example of the information display threshold table generated in the processing for generating the information display threshold value table.

FIG. 11 is a table illustrating an example of the information display threshold value table when an information display threshold value relative to a position is individually set in the clinical record data of a patient.

FIG. 12 is a table illustrating an example of the information concealing level table when an information concealing level of a specific image 501 is set to 80.

FIG. 14 is a table illustrating an example of the information concealing level table when the information concealing level of a word "neuropsychiatric disease" is set to 80 in columns of a disease name and finding.

DESCRIPTION OF THE EMBODIMENTS

Preferred embodiments of the present invention will now be described in detail in accordance with the accompanying drawings.

Embodiments of the present information will be described below. In each of the embodiments of the present invention, "medical information" refers to information relating to medical practice such as medical examination histories, examination histories, search result lists of examination items and the like. In the embodiments below, a doctor is assumed to be an example of a user (operator), and a house visit by the doctor is assumed in the description. However, the user is not limited to the doctor, and the present invention is similarly available for nurses and carers who go for home-visit care. Moreover, a technical range of the present invention is not limited to each of the following embodiments.

First Embodiment

Figure 1:
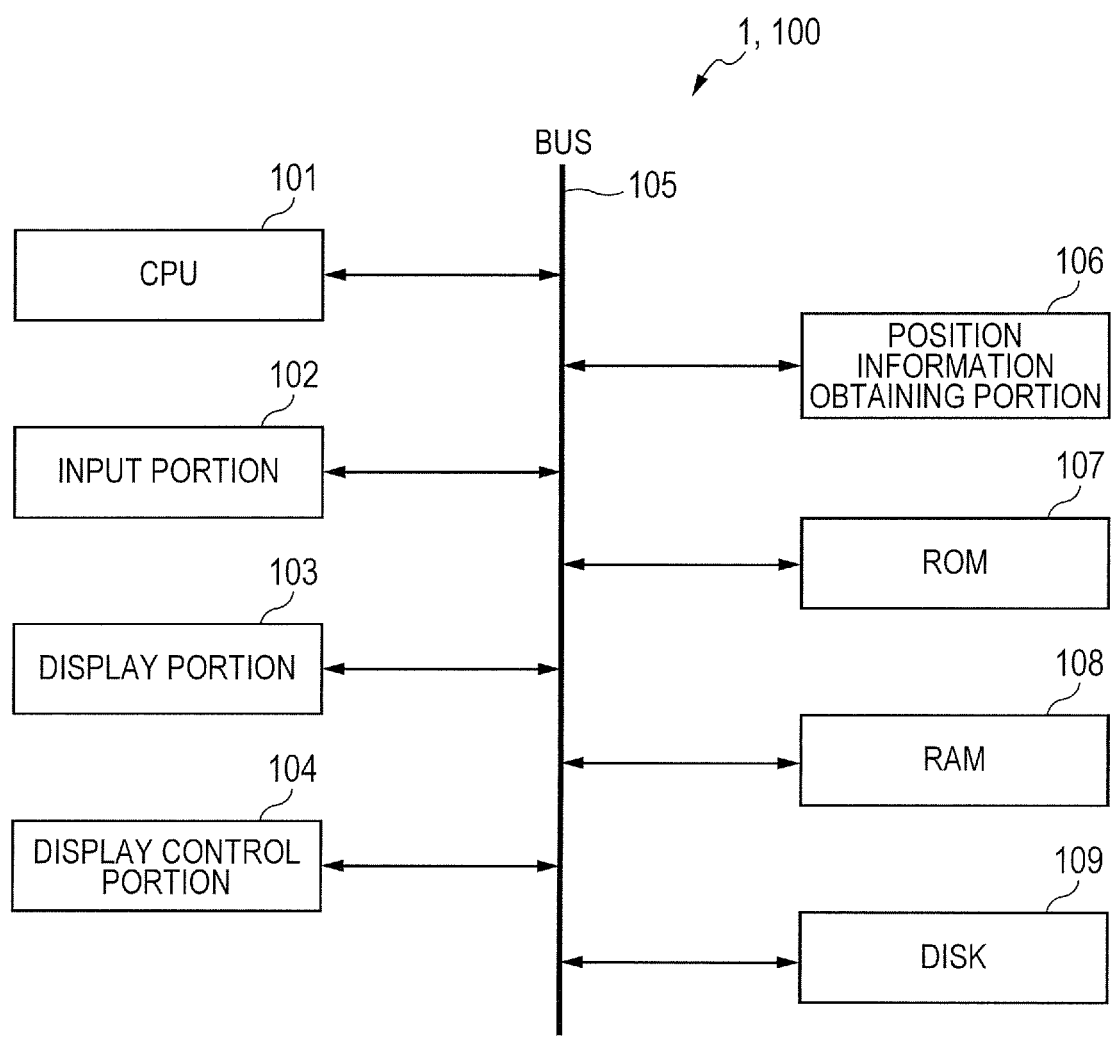
FIG. 1 is a block diagram illustrating an outline configuration of a medical information concealing system provided in a medical information terminal according to an embodiment of the present invention.

First, a first embodiment of the present invention will be described by using the attached drawings and flowcharts. FIG. 1 is a block diagram illustrating an outline configuration of a medical information concealing system 100 provided in a medical information terminal 1 which is the first embodiment of the present invention (hereinafter simply referred to as "medical information concealing system 100").

As illustrated in FIG. 1, the medical information concealing system 100 includes a CPU 101, an input portion 102, a display portion 103, a display control portion 104, a BUS 105, a position information obtaining portion 106, a ROM 107, a RAM 108 and a DISK 109.

The CPU 101 is a central processing unit and totally controls each portion which will be described below.

The input portion 102 is a button, a keyboard, a touch panel or the like into which the user inputs various instructions. The various instructions input in the input portion 102 are transmitted to the CPU 101. The CPU 101 executes processing according to the instructions input in the input portion 102.

A liquid crystal display or the like is applied to the display portion 103, and the display portion 103 can display medical practice records of a patient.

The display control portion 104 controls contents to be displayed on the display portion 103 based on current position information of the medical information terminal 1 obtained by the position information obtaining portion 106.

The BUS 105 is a communication bus which is a transfer path of various types of data. For example, a signal of an instruction to each portion (each device) to be controlled from the CPU 101 and data between the portions are transferred to a predetermined processing portion.

The position information obtaining portion 106 is a GPS (Global Positioning System) and measures a position of the medical information terminal 1 by latitude and longitude and generates position information (GPS information) indicating the current position.

The ROM 107 is a read-only nonvolatile memory. The ROM 107 stores a boot program executed by the CPU 101, a control program of the medical information concealing system 100, and various initial data referred to in various types of processing.

The RAM 108 is a readable/writable random-access memory and is used for temporary storage of various types of data from each portion. The RAM 108 stores various work regions which store data required for the processing, stacks required during the processing and various types of data whose values are changed during the processing. An information concealing level table and an information display threshold value table, which will be described later, are stored or configured in the RAM 108.

The DISK 109 is a mass storage device and changeably stores a large volume of data. The DISK 109 is constituted by a hard disk and an SSD, for example.

Computer programs such as the boot program and the control program for controlling the medical information terminal 1 including the medical information concealing system 100 are stored in the ROM 107 in advance. The CPU 101 reads the computer programs from the ROM 107 and executes them. As a result, control of each portion is executed, and the following processing and operations are realized. The computer programs such as the boot program and the control program executed by the CPU 101 and various types of initial data to be referred to during execution of these programs are loaded to a temporary storage unit illustrated as the RAM 108 as necessary and executed or referred to. In this way, the computer programs and initial data can be modified in the middle instead of fixing them, and a flexible system can be realized. Moreover, upon end processing such as powering-off of the medical information terminal 1, the CPU 101 stores the information concealing level table and the information display threshold value table stored in the RAM 108 in the DISK 109 in a process of the end processing. The CPU 101 reads the tables stored in the DISK 109 into the RAM 108 at the subsequent start. As a result, the doctor as a user can start using the terminal in a previously halted state.

Subsequently, an example of a flow of preparation for a house visit by a doctor will be described. It is assumed that an electronic clinical record system in which clinical records of patients are computer-readably stored is configured in a hospital, and that a doctor who is a user can copy the clinical record data of a patient stored in this electronic clinical record system to the medical information terminal 1.

Figure 2:
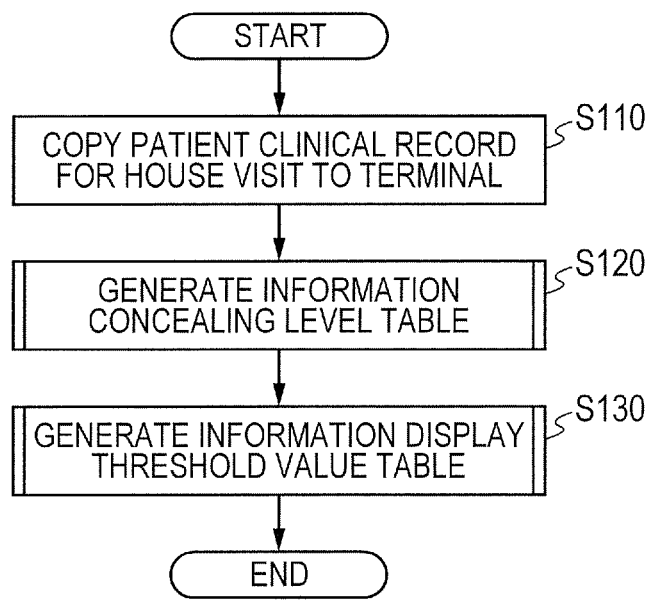
FIG. 2 is a flowchart illustrating an example of an operation of the medical information concealing system in preparation for a house visit.

FIG. 2 is a flowchart illustrating an operation example of the medical information terminal 1 when the doctor sets medical information terminal 1 to be brought with him/her before going out for a house visit.

At Step S110, the CPU 101 takes out clinical record data of a patient, who is a target for a house visit, from an electronic clinical record system in a hospital to the DISK 109 and copies the data to the medical information terminal 1 to be taken to the house visit destination. Specifically, first, the doctor inputs an instruction of copying the clinical record data of the patient into the input portion 102. Upon detection of the input of the instruction into the input portion 102, the CPU 101 executes this processing.

At generation of an information concealing level table at Step S120 (information concealing level setting), the CPU 101 determines the information concealing level for each item in the clinical record data of the patient and generates an information concealing level table in which each item is associated with an information concealing level. Contents of this processing of generating the information concealing level table (information concealing level setting) will be described later.

At Step S130 (information display threshold value table generation), the CPU 101 generates an information display threshold value table in which position information of the house visit destination is associated with an ID of the patient present at the house visit destination. Contents of this processing of generating the information display threshold value table will be described later.

Thus, the processing of preparation for the medical information terminal 1 before a doctor goes out for a house visit is completed.

Figure 3:
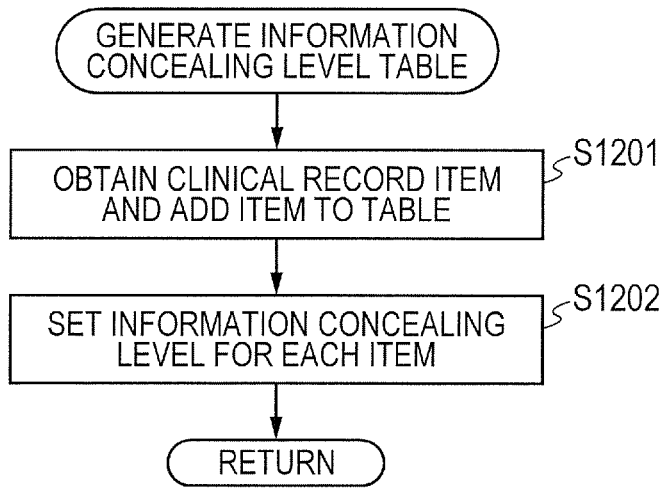
FIG. 3 is a flowchart illustrating an example of processing for generating an information concealing level table.

Subsequently, the contents of the processing of generating the information concealing level table (information concealing level setting) will be described by referring to FIGS. 3 and 4. FIG. 3 is a flowchart illustrating processing contents of the information concealing level table generation (information concealing level setting) at Step S120 in FIG. 2. FIG. 4 is a diagram illustrating an example of the information concealing level table generated by the processing of generating the information concealing level table at Step S120.

At Step S1201, the CPU 101 obtains item names such as "name" and "disease name" from the clinical record data of the patient having been copied to the DISK 109 and adds the obtained item names to the information concealing level table.

At Step S1202, the CPU 101 determines the information concealing level of each of the items added to the information display threshold value table and applies the determined information concealing level to the information concealing level table. The information concealing level is a numeral value indicating a degree that the information should not be seen by a third party other than the doctor and the patient himself/herself. The larger this numeral value is, the higher the degree that the information should not be seen by a third party other than the doctor and the patient himself/herself is. As a method of determining the information concealing level, such method can be applied that a default value of the information concealing level of each item is stored in the ROM 107 in advance, and the default value is determined as the information concealing level for each item. The default value is set according to a content of each item and the like as appropriate. If the doctor would like to give a high level of privacy protection, the doctor may edit the information concealing level table and execute processing of changing the information concealing level of a specific item. In this case, the CPU 101 has the display portion 103 display a menu for editing the information concealing level table. The doctor inputs the information concealing level of the specific item into the input portion 102 according to this displayed menu. The CPU 101 applies the information concealing level input into the input portion 102 to the information concealing level table. By having the doctor change the information concealing level as above, the information concealing level according to circumstances specific to doctors can be set. Therefore, flexibility of the medical information concealing system 100 can be improved.

FIG. 4 illustrates an example in which the information concealing level is 80 for the name, address, telephone number and date of birth, 70 for a disease name and a medicine name and 50 for a diagnosis image.

Figure 5:
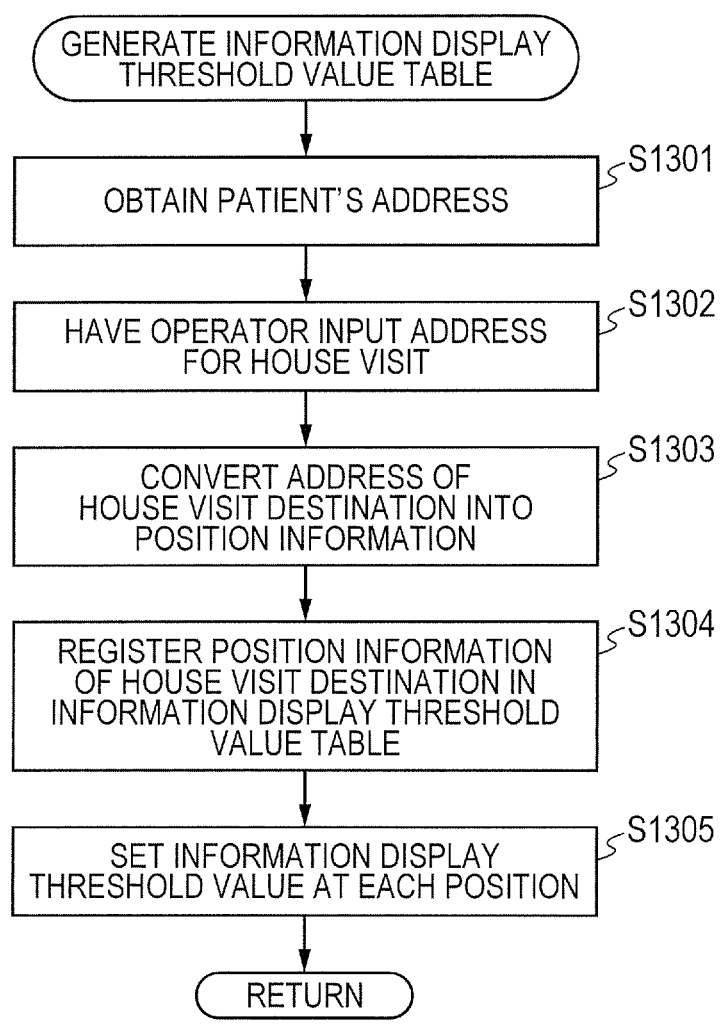
FIG. 5 is a flowchart illustrating an example of processing for generating an information display threshold value table.

Subsequently, processing contents of the information display threshold value table generation at Step S130 will be described by referring to FIGS. 5 and 6. FIG. 5 is a flowchart illustrating processing contents of the information display threshold value table generation at Step S130 in FIG. 2. The information display threshold value table is a table illustrating correspondence between position information indicating a position of a house visit destination and an information display threshold value at the house visit destination. FIG. 6 is a diagram illustrating an example of a configuration of the information display threshold value table. The information display threshold value table associates the position information which is a combination of latitude and longitude with the information display threshold value at that position. If an instruction to browse clinical record data is input into the input portion 102, the CPU 101 compares a current position information in the medical information terminal 1 with position information of the information display threshold value table in order from upper entries. Then, the CPU 101 uses the information display threshold value associated with any matched position information in clinical record information concealing display processing (which will be described later). On the other hand, if there is no matching, the CPU 101 uses a default information display threshold value in the clinical record information concealing display processing.

A method of generating this information display threshold value table will be described.

At Step S1301, the CPU 101 obtains a patient's address from clinical record data copied to the DISK 109.

At Step S1302, the CPU 101 executes processing of prompting a doctor (user) of the medical information terminal 1 to set an address of a house visit. For example, the CPU 101 has the display portion 103 display a screen for input and confirmation of the house visit destination. The doctor inputs the house visit address into the input portion 102 according to the display on the display portion 103. If the actual house visit address is identical with the patient's address obtained at step S1301, the address may be used as the house visit address. However, if the house visit address is different from the patient's address for some reason of the patient, if the patient is resident in a nursing home for elderly, or the like, the actual house visit address needs to be corrected. Thus, at Step S1302, the doctor (user) checks and corrects the actual house visit address. The CPU 101 sets the house visit address input into the input portion 102 to a house visit address used in processing at Step S1303 and Step S1305 described below.

At Step S1303, the CPU 101 converts the house visit address set at Step S1302 to position information which is a combination of latitude and longitude.

At Step S1304, the CPU 101 registers the position information of the patient's house visit address in the information display threshold value table.

At Step S1305, the CPU 101 sets an information display threshold value to each piece of the position information in the information display threshold value table.

An example of a flow of preparation before house visit has been described.

Figure 7:
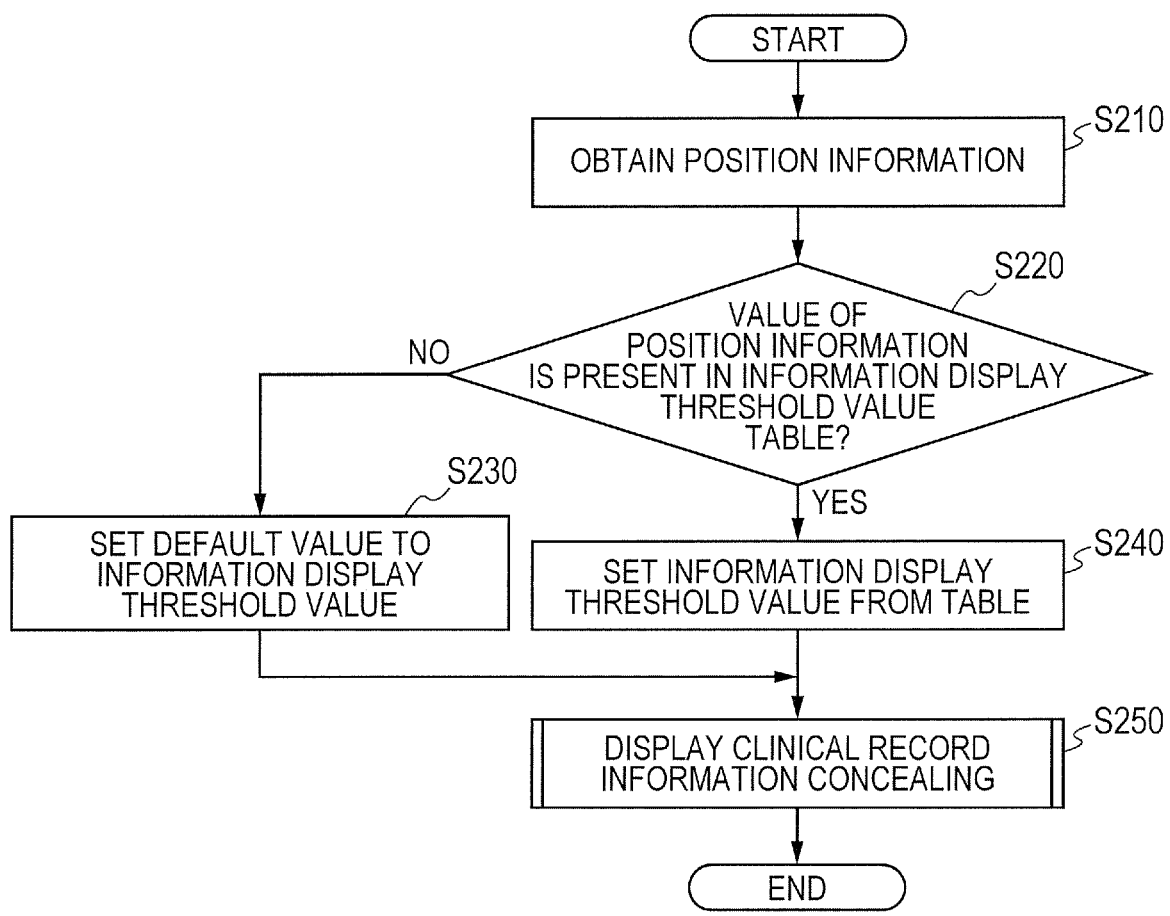
FIG. 7 is a flowchart illustrating an example of an operation of the medical information concealing system when medical information is browsed.

Subsequently, a flow of an operation of the medical information concealing system 100 when the medical information is browsed by using the medical information terminal 1 carried by the doctor for the house visit will be described. FIG. 7 is a flowchart illustrating an operation example when the patient clinical record information is browsed using the medical information terminal to be carried to the house visit.

At Step S210, the CPU 101 obtains position information (GPS information) indicating a current position of the current medical information terminal 1 from the position information obtaining portion 106.

At Step S220 (condition determining step), the CPU 101 determines whether or not the position information (GPS information) obtained by the position information obtaining portion 106 at Step S210 is present in the information display threshold value table. In this determination, allowance for some degree of an accuracy error may be set. For example, determination criteria may be such that the position indicated by the position information obtained by the position information obtaining portion 106 is within a radius of 50 meters from the position indicated by the position information registered in the information display threshold value table. As a result, an error caused in the position information obtaining portion 106 of the terminal when the position information is obtained can be allowed to some degree.

If it is determined that the position information obtained by the position information obtaining portion 106 is present in the information display threshold value table, the routine proceeds to Step S240, while if it is determined as not, the routine proceeds to Step S230.

At Step S230, the CPU 101 determines a default value to be the information display threshold value. On the other hand at Step S240, the CPU 101 determines an information display threshold value corresponding to the current position information from information display threshold values set in the information display threshold value table to be the current information display threshold value.

At Step S250 (clinical record information concealing display processing), the CPU 101 displays the information in the clinical record data at the information display threshold value or more for which the information concealing level is currently set on the screen in a concealed state.

Figure 8:
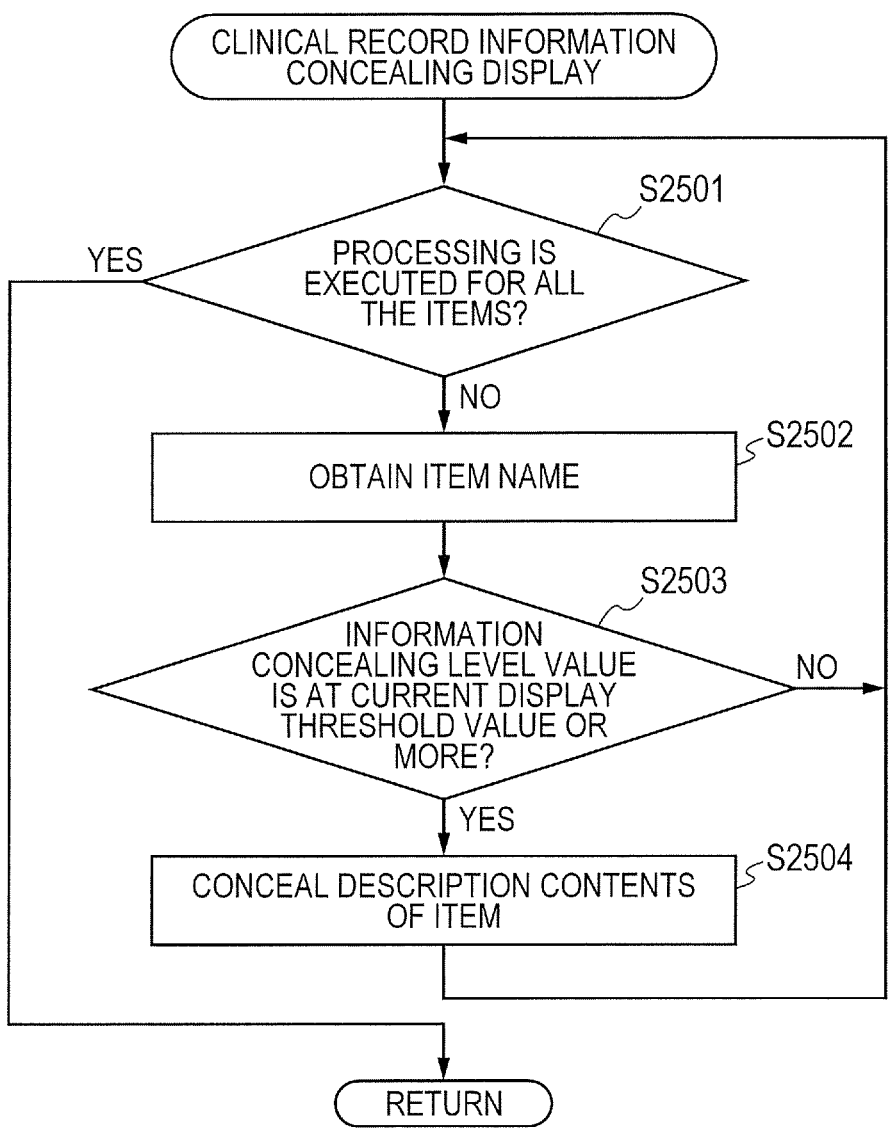
FIG. 8 is a flowchart illustrating an example of clinical record information concealing display processing.

Here, the clinical record information concealing display processing will be described by referring to FIG. 8. FIG. 8 is a flowchart illustrating an example of processing contents of the clinical record information concealing display at Step S250 in FIG. 7.

At Step S2501, the CPU 101 determines whether or not the processing at Steps S2502 to S2504 described below has been executed for all the items in the clinical record data. If it is determined at Step S2501 that the processing has been executed for all the items in the clinical record data, the clinical record information concealing display processing is finished. If it is determined at Step S2501 that an item for which processing has not yet been executed remains in the clinical record data, the processing proceeds to Step S2502.

At Step S2502, the CPU 101 obtains item names to be subsequently processed from the clinical record data. The item names here include "name," "disease name," "diagnosis image" and the like.

At Step S2503, the CPU 101 searches the information concealing level table generated at Step S120 before the house visit and obtains an information concealing level associated with the item name obtained at Step S2502. Then, the CPU 101 determines whether or not the obtained information concealing level is at the current information display threshold value or more. If the obtained information concealing level is not more than the current information display threshold value, the routine proceeds to Step S2501 without executing the processing at Step S2504 for the item. On the other hand, if the obtained information concealing level is at the current information display threshold value or more, the routine proceeds to Step S2504.

At Step S2504, the CPU 101 executes concealing processing for a description content of each item.

The description content here refers to the actual name of the patient and the disease input for the item names "name" and "disease name" in the clinical record data. In the case of an item such as the disease name in which plural entries can be input, all the information input in the column "disease name" is the description content. That is, the past disease names of the patient are all subjected to the concealing processing as the description content. In addition, in the case of an item such as the item name "finding" in which the doctor writes sentences, the whole sentences written in the finding column are the description content of the item name "finding." Moreover, in the case of an item such as the item name "diagnosis image" containing data other than text data, all the images pasted in the "diagnosis image" item in the patient clinical record data are the description content of the item name "diagnosis image."

At this Step S2504, the CPU 101 executes concealing processing for the description contents. A method of encryption, ciphering, non-display or the like is applied as the concealing processing method, here, if the description contents are text data. In the encryption method, a hash function may be provided in the medical information terminal 1 and applied to the description contents to be concealed. In the ciphering, the description contents to be concealed may be replaced with a character like "*". In the non-display, the description contents to be concealed may be replaced with blank characters. If the description contents are those other than text data such as the "diagnosis contents," the non-display method is applied as the method of concealing processing. As the method of concealing processing for image data, first, the CPU 101 generates image data having the same lateral and vertical sizes as those of the image data to be concealed and painted in the same color as a background color of the screen on the display portion 103. Then, the CPU 101 controls the display control portion 104, and the display control portion 104 has the display portion 103 display the generated image data on a target image in an overlapping manner according to the control by the CPU 101. Other concealing processing methods may be used other than the above as long as browsing of the information displayed on the display portion 103 of the medical information terminal 1 (description contents of each item) is made difficult.

The flow of browsing of medical information has been described.

According to a configuration of the first embodiment, when the doctor browses the clinical record data of a patient by using the medical information terminal on the way to a house visit destination, the medical information terminal 1 displays items having an information concealing level at the information display threshold value or more according to the position in a concealed manner. As a result, browsing can be made by giving consideration to privacy of the patient. Therefore, possibility of leakage of patient personal information can be reduced in the case of peeping by a third party or loss of the medical information terminal 1. Moreover, since the doctor browses the clinical record data of the patient to visit while moving, efficiency of medical examination at the actual visit is improved.

Second Embodiment

In the first embodiment, the methods of encryption, ciphering, non-display and the like of the description contents are used as the medical information concealing method. On the other hand, in the second embodiment, a method of non-display of a portion to be concealed, and enlarging and displaying a diagnosis image on that portion is used as another concealing method.

Figure 9:
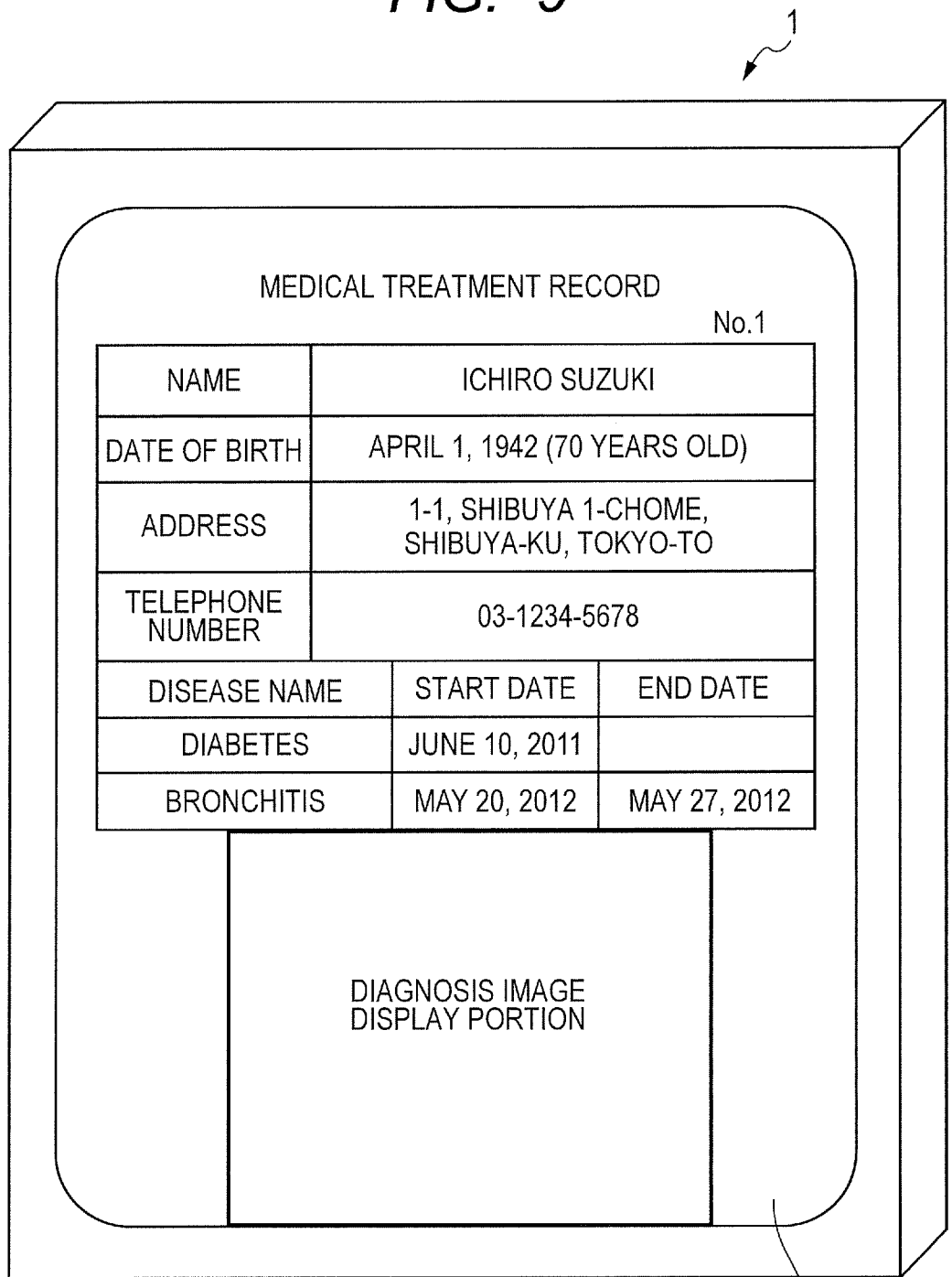
FIG. 9 is a diagram illustrating an example of display on a display portion when a medical information terminal is in a hospital or the like and all information in a clinical record data can be browsed.

FIG. 9 illustrates an example of the display portion 103 of the medical information terminal 1. FIG. 9 illustrates a situation as in a hospital in which the information display threshold value is high and all the information included in the patient clinical record data (description contents) is seen. On a house visit, at a place other than the hospital and the house visit destination, the information concealing level of the items such as name, date of birth, address and telephone number rises to the information display threshold value or more and the information is concealed.

Figure 10:
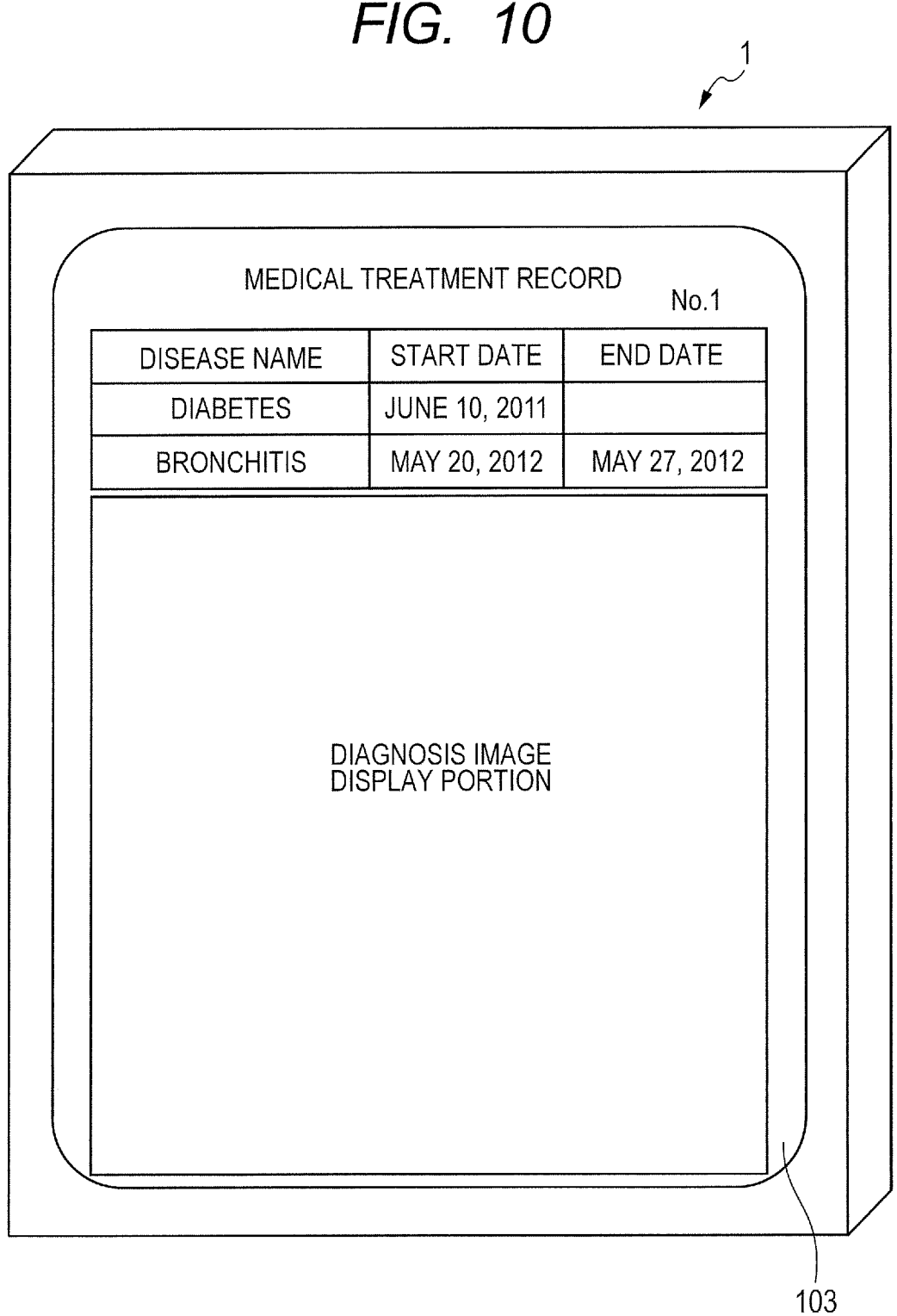
FIG. 10 is a diagram illustrating an example of display on the display portion when the medical information terminal is at a position other than in the hospital and the house visit destination and some pieces of the information in the clinical record data are concealed.

Information cannot be obtained from the concealed item during browsing. Thus, in order to effectively use the space, the display control portion 104 displays the diagnosis image in an enlarged manner as non-concealed information according to control by the CPU 101. Then, the display portion 103 displays the diagnosis image in an enlarged manner as illustrated in FIG. 10 according to the control by the display control portion 104. FIG. 10 is an example of concealing the name, date of birth, address and telephone number from the state in FIG. 9, and displaying the diagnosis image in an enlarged manner by using the spaces thereof. As a result, the doctor can check a symptom in advance easily.

Here, a configuration of enlarged display of a diagnosis image is illustrated in order to effectively use a space for displaying concealed description contents. However, an item to be enlarged does not have to be a diagnosis image. For example, the entire character size may be enlarged and the character size of a portion in which long sentences are written such as the past diagnosis records may be enlarged so that the display can be seen more easily. With these configurations as well, the same advantages as those of the above enlarged display of the diagnosis image can be obtained.

According to the configuration of the second embodiment, by enlarging and displaying the non-concealed information, the concealed information is hidden and non-concealed browsable information can be displayed to be seen easily.

Third Embodiment

The first embodiment has the configuration in which the information display threshold value table is generated so that the information display threshold value is uniquely determined according to the position. On the other hand, a third embodiment has a configuration in which the information display threshold values are provided in plural stages.

For example, the CPU 101 sets the information display threshold value to 100 at the hospital and the house visit destination in the processing of information display threshold value table generation (S130 in FIG. 2) and to 75 at positions other than those. Moreover, the CPU 101 provides an authentication mechanism such as a password (executes authentication processing), and if the authentication is successful, the CPU 101 executes processing of raising the information display threshold value to 90. That is, the display control portion 104 has the display portion 103 display for prompting the doctor to input a password according to the control by the CPU 101. Then, the doctor inputs the password into the input portion 102. The CPU 101 determines whether or not the password input into the input portion 102 matches the password set in advance, and if matched, the authentication is successful. As a result, the doctor can see some of the concealed items by authentication using a password or the like after checking no one is around him/her.

Moreover, there can be an operation method of raising the information display threshold value by authentication using a password or the like at a house visit destination in the case of a house visit where there are many people other than the patient such as a nursing home. For example, the information display threshold value at a hospital is set to 100, the information display threshold value at a nursing home as the house visit destination to 90, and the information display threshold value at positions other than those to 75. As a result, browsing at the house visit destination requires security higher than that in the hospital. Then, a password can be input to raise the information display threshold value from to 100 at the nursing home for the house visit. By operating as above, even if the medical information terminal 1 is left behind at the nursing home at the house visit destination, possibility that the item with a high information concealing level is browsed by a third party can be reduced.

Fourth Embodiment

In the first embodiment, the information display threshold value is set to 100 at the house visit destination and all the clinical record data of a patient in the medical information terminal 1 can be browsed. In the fourth embodiment, the CPU 101 adds an item of a patient clinical record ID to the information display threshold value table in the first embodiment and associates the patient clinical record data with the position ID. As described above, in the fourth embodiment, the information display threshold value table in which the position ID is associated with the patient clinical record data is configured. When the CPU 101 controls the display control portion 104 to have the display portion 103 display information, the information display threshold value set in the information display threshold value table is individually applied only to the patient clinical record data associated with the current position information of the medical information terminal 1. On the other hand, when another patient clinical record data is to be displayed, the CPU 101 uses a default value for the information display threshold value. As described above, the CPU 101 sets the information display threshold value in the information display threshold value table individually for each patient depending on the position of the medical information terminal 1.

FIG. 11 is a diagram illustrating an example of the information display threshold value table generated in the fourth embodiment. In the fourth embodiment, the CPU 101 generates the information display threshold value table as in FIG. 11. It is different from the information display threshold value table in the first embodiment (see FIG. 6) in configuration in that the patient clinical record ID (patient clinical record data) is associated with the position ID. The CPU 101 determines whether or not the position of the medical information terminal 1 matches any of the position information in the information display threshold value table. If it is determined to match, the CPU 101 uses the information display threshold value set in the generated information display threshold value table for the associated patient clinical record data in the clinical record information concealing display processing. On the other hand, if the clinical record data of the non-associated patient clinical record ID is to be displayed, the CPU 101 uses the default information display threshold value in the clinical record information concealing display processing.

Here, the processing of the medical information terminal 1 according to the fourth embodiment and an example of an actual use mode will be described specifically for a case in which the information display threshold value table in FIG. 11 is prepared. Here, it is assumed that the doctor is visiting two patients described in patient clinical record IDs 401 and 402, respectively, for house visits. A position ID 1 in FIG. 11 indicates a position in a hospital, and the information display threshold values for the patient clinical record IDs 401 and 402 are set to 100. A position ID 2 and a position ID 3 are house visit destinations of the patients described in the patient clinical record IDs 401 and 402, respectively. First, if the medical information terminal 1 is located in the hospital (position ID:1), the CPU 101 determines that the position ID at the current position of the medical information terminal 1 is 1 based on the position information obtained by the position information obtaining portion 106. Thus, the CPU 101 sets the information display threshold value of the patient clinical record IDs 401 and 402 to 100. Therefore, the doctor can browse the description contents of the clinical record data for both the patient clinical record IDs 401 and 402 with the information display threshold value at 100 inside the hospital.

When the doctor carries the terminal to the position matching the position ID 2 and makes a house visit, the CPU 101 executes processing of setting the information display threshold value based on the position information obtained by the position information obtaining portion 106. In this example, since the medical information terminal 1 is located at the position ID 2, the information display threshold value of the clinical record data of the patient clinical record ID 401 is set to 100, and the information display threshold value of the clinical record data of the patient clinical record ID 402 is set to 75. Thus, the doctor can browse the patient clinical record ID 401 with the information display threshold value at 100. At that time, since the default value of 75 is used as the information display threshold value during browsing of the clinical record data other than the patient clinical record ID 401, the items with the information concealing level not lower than 75 cannot be browsed.

According to such configuration, possibility that important medical information of other patients is seen can be reduced when the doctor or the like leaves the medical information terminal 1 at a patient's house.

Fifth Embodiment

The first embodiment described above is configured such that the information concealing level is set for each item in the information concealing level table. That is, even if a plurality of description contents are included in one item, the same information concealing level is set for all the description contents included in the one item. Thus, with this configuration, all the description contents included in one item are concealed or all are displayed. However, even if the doctor determines that the item may be basically displayed at a house visit, a part of the description contents may be desirably concealed. For example, if the "disease name" is set so as to be displayed outside of the hospital, past diseases unnecessary at this house visit are also displayed. Patients would not like a third party to know some of the disease names, and display of all of them is not desirable. In addition, if the item name "diagnosis image" is set to be displayed also outside of the hospital and if the face of a patient is included in a specific image of the diagnosis images, display of such image outside of the hospital is not desirable. The fifth embodiment has a configuration which enables concealing of a specific part of the description contents in some items in such cases.

For example, it is assumed that the information concealing level table as illustrated in FIG. 4 is generated as in the example cited in the first embodiment. Specifically, the information concealing levels of the name, address, telephone number and date of birth are set to 80, the information concealing levels of the disease name and medicine name are set to 70, and the information concealing level of the diagnoses image is set to 50. The information display threshold value is set to 100 inside the hospital and at the patient's house and to 75 at positions other than them. In such a case, the items of the name, address and telephone number at the information display threshold value of 75 or more are automatically concealed at positions other than the hospital and the patient's house. However, the disease name and the medicine name have the information concealing levels of 70 and the diagnosis image has the information concealing level of 50, their description contents are displayed. A diagnosis image showing the face might lead to identification of the person. Thus, when the clinical record data is copied to the terminal so as to generate the information concealing level table, the information concealing level for this diagnosis image may be individually set higher.

FIG. 12 illustrates an example of the information concealing level table in the fifth embodiment. In the information concealing level table in the fifth embodiment, a "designation target" is added as compared with the information concealing level table in the first embodiment. In the designation target, description contents for which the information concealing level is to be set higher is designated in the plurality of description contents belonging to a target item. In the example illustrated in FIG. 12, a plurality of images belong to the item of "diagnosis image," and an "image 501" in the plurality of images is indicated as the description contents for which the information concealing level is to be set higher.

For example, it is assumed that a plurality of images are included in the clinical record data of a patient in the electronic clinical record system in a hospital, and the "image 501" among them is a photo of the face of the patient. Also, it is assumed that when the doctor copies the clinical record data to the medical information terminal 1, the doctor determines that the "image 501" is the photo of the face so that it is not desirable to display it while the doctor moves to the house visit destination. In this case, the doctor performs an operation of newly adding an item of the "diagnosis image" by using the input portion 102. Specifically, the doctor performs an operation of designating the "image 501" for the target designation of the added "diagnosis image" and an operation of setting the information concealing level of the added "diagnosis image" to a value (80 in this example) higher than the information concealing level (50 in this example) of the item of the existing "diagnosis image." Then, the CPU 101 edits the information concealing level table according to the operations on the input portion 102 by the doctor. That is, the CPU 101 newly adds the item of the "diagnosis image" to the information concealing level table, designates the "image 501" for the designation target of the added item of the "diagnosis image" and sets the information concealing level of the item for which the "image 501" is designated to 80.

This operation and processing may be executed after the processing illustrated in FIG. 2 is finished or may be executed in the process of the information concealing level table generation processing illustrated in FIG. 3.

In the clinical record information concealing display processing, the CPU 101 compares the information concealing level (50 in this example) of the diagnosis image, that is, the item to which the "image 501" belongs, with the information concealing level (80 in this example) of the image 501 itself. Then, the CPU 101 determines the higher information concealing level to be the information concealing level of the "image 501." In this example, the CPU 101 assumes that the information concealing level of the "image 501" is 80 and compares the level with the information display threshold value and determines whether or not to display the "image 501." In this example, though the information concealing level of the image 501 is 80, the information display threshold value at positions other than the hospital and the house visit destination is 75. Thus, the CPU 101 does not display the contents of the "image 501" and thus, patient privacy can be protected.

As described above, the description contents belonging to an item are basically displayed, but a specific part of the description contents in the plurality of description contents belonging to the item can be concealed without displaying all of them. Thus, patient privacy can be protected while convenience of information browsing of patient clinical record data while the doctor moves to the house visit destination is kept high.

The example described above is configured such that the diagnosis image is designated as a target for concealing, and the information concealing level is set on a per image basis. However, the target of concealing is not limited to images. In addition, a specific portion in the description contents of an item described in text might be concealed. The disease name not directly related to the house visit then or a disease name such as an infectious disease that would heighten anxiety if known to residents in the neighborhood of the house visit destination, should not be displayed at a position where a third party other than the doctor and the patient can see. Moreover, the medicine names for those diseases should not be displayed since the disease names might be known.

Figure 13:
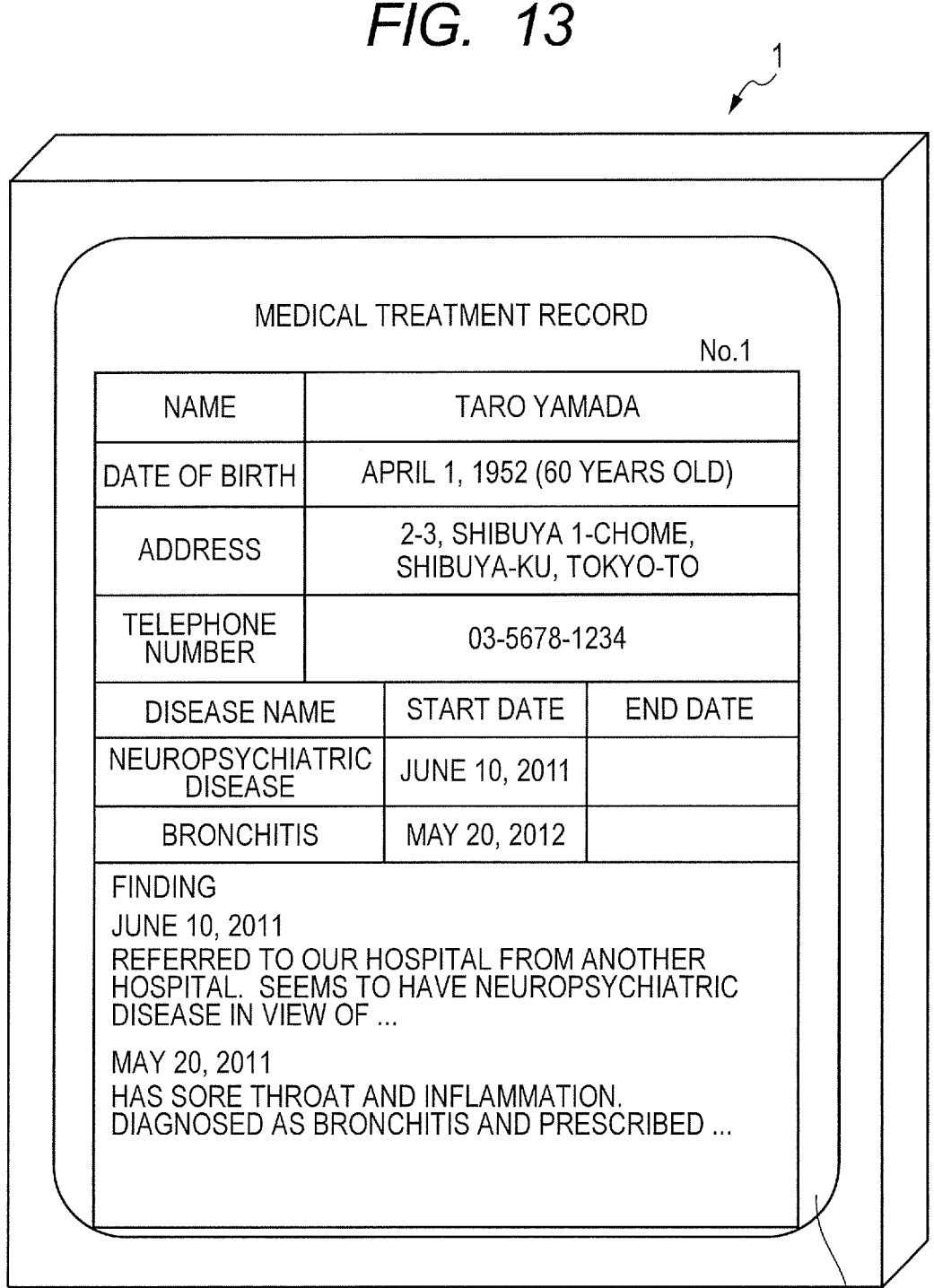
FIG. 13 is a diagram illustrating an example of display on the display portion of the medical information terminal when the medical information terminal is in the hospital and the like and all the information in the clinical record data can be browsed.

For example, FIG. 13 illustrates a case in which the clinical record data of a patient having "neuropsychiatric disease" and "bronchitis" as the current diseases is displayed in a hospital. It is assumed that the doctor is going for a house visit to treat the "bronchitis" for this patient. At this time, it is assumed that the information concealing level for the name, address, telephone number and date of birth is set to 80, the information concealing level for the disease name and medicine name to 70 and the information concealing level for the finding is set to 50. Also it is assumed that the information display threshold value inside the hospital and at the patient's house is set to 100 and the information display threshold value at other positions to 75. With such setting, the items of disease name, medicine name and finding can be browsed outside of the hospital. It is assumed that when the clinical record data is copied to the medical information terminal 1 during preparation for a house visit, the doctor determines that the "neuropsychiatric disease" is not directly needed for the house visit and should not be displayed outside of the hospital. In such a case, the doctor performs an operation of editing the information concealing level table and adds the "neuropsychiatric disease" to the target designation portions of the "disease name" and "finding" in which the "neuropsychiatric disease" is described as illustrated in FIG. 14 and designates the information concealing level at 80. The CPU 101 sets the information concealing level of the "neuropsychiatric disease" which is the target designation added to the information concealing level table according to the operation by the doctor to 80.

Then, in the information concealing display processing, the CPU 101 sets the character strings of the "neuropsychiatric disease" set as the target designation to be concealed. That is, the CPU 101 uses the newly added and set information concealing level (80 in each case) in determination on whether the character strings of the "neuropsychiatric disease" included in the description contents of the disease name and finding are to be displayed or not.

Figure 15:
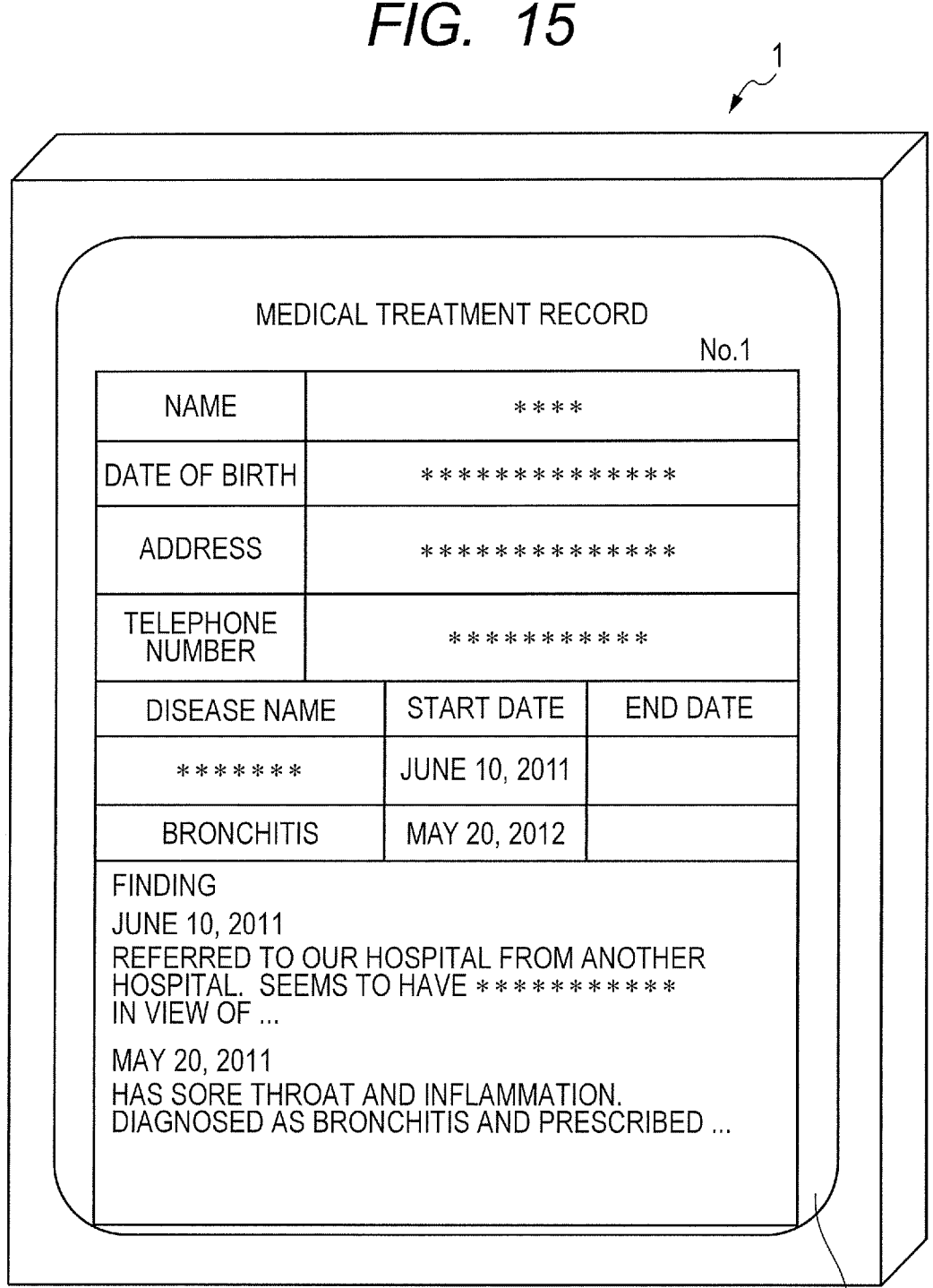
FIG. 15 is a diagram illustrating an example of display on the display portion at a destination of a visit when the information concealing level table is set as in the example illustrated in FIG. 14.

With such setting, at a position where the information display threshold value set based on the position information is larger than 80, the character strings of "neuropsychiatric disease" in the "disease name" and "finding" are concealed, and display is shown as in FIG. 15. FIG. 15 is a diagram illustrating an example of display on the display portion 103 at the position where the information display threshold value set based on the position information is larger than 80. In the example illustrated in FIG. 15, the example in which a character string of the "neuropsychiatric disease" is replaced with a character string of "*****" is illustrated. Other than that, the character strings of the "neuropsychiatric disease" may be replaced with a blank.

As described above, by concealing the specific character strings in the description contents of an item, patient privacy can be protected while convenience of information browsing of the patient clinical record data can be kept high similarly to the configuration using the image as the target.

Sixth Embodiment

A sixth embodiment is configured such that the information concealing level of the specific description contents such as those cited in the fifth embodiment is set automatically based on an onset risk rate of a disease and a use frequency of a drug.

The DISK 109 stores a database including disease names and their onset risk rates and a database including the drug names and their use frequencies in advance. In the information concealing level table generation processing, the CPU 101 reads out the contents of the databases and determines whether or not there is an onset risk rate of the disease name or a use frequency of the drug name matching the description contents of the item name "disease name" and "medicine name." If there is the matching disease name or medicine name, the CPU 101 sets the information concealing level according to the onset risk rate and the use frequency stored in the databases.

According to such configuration, the number of times of setting sessions by the doctor for the information concealing level of a specific description content is reduced. Therefore, a burden on preparation for a house visit by the doctor can be alleviated.

Moreover, a table individually setting the concealing levels for some disease names and medicine names may be stored in the DISK 109 in advance. In this case, in the information concealing level table generation processing, the CPU 101 executes processing of reading out the contents of the table and checking the read-out contents with the description contents of each item. If there are description contents matching the read-out contents as the result of checking processing, the CPU 101 adds the item name to which the description contents belong, to the information concealing level table. Moreover, the CPU 101 sets the description contents for the designation target of the added item name and sets the information concealing level of the description contents to a value set in the read-out table. According to such configuration, even if the use frequency or onset risk rate is not stored in the database, the number of times of setting sessions by the doctor for the information concealing level of a specific description content can be reduced.

Exemplary embodiments of the present invention have been described, but the present invention is not limited to these embodiments and capable of various modifications and changes within a range of the gist thereof.

For example, in the embodiments, encryption, ciphering, non-display and overlapped display are indicated as the methods of concealing medical information, but the present invention is not limited to these methods.

Furthermore, in the embodiments, the position information obtaining portion has been discussed with the use of the GPS (Global Positioning System), but the present invention is not limited to the arrangements with the GPS. For example, it is possible to obtain the position information using the LCS (Location Service) protocol of the LTE (Long Term Evolution) communication standard. Some positioning methods are defined in the LCS, including a method of determining the position of a terminal by means of the difference between arrival times of signals received at the terminal from a plurality of base stations. In this way, it is possible to determine the latitude and longitude of the terminal with the position information obtained by the LCS, as is the case with the position information in the GPS. The embodiments discussed above therefore can be realized with the position information obtained by the LCS as well.

Other Embodiments

The present invention is realized also by executing the following processing. That is, software (program) for realizing the function of the aforementioned embodiments is supplied to a network or a system or an apparatus through various storage media, and a computer (or a CPU, MPU and the like) of the system or the apparatus reads out a program code and executes processing. In this case, the program and the storage medium storing the program constitute the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-288607, filed Dec. 28, 2012, which is hereby incorporated by reference herein in its entirety.

What is claimed is:

1. A portable medical information terminal capable of displaying medical information which is personal information of a patient comprising:

at least one memory storing (a) the medical information including a plurality of items, (b) a plurality of information concealing levels corresponding to each of the plurality of items included in the medical information, and (c) a program;

at least one processor which, by executing the program, functions to:

in a case where the medical information is browsed by a user, obtain position information indicating a current position of the portable medical information terminal; and determine whether a display unit displays each of the plurality of items included in the medical information by comparing a plurality of previously set position information corresponding to the plurality of information concealing levels of each of the plurality of items included in the medical information with the position information indicating the current position of the portable medical information terminal.

2. The portable medical information terminal according to claim 1, wherein in a case where the current position is a first position, the display unit does not display the item of which information concealing level is a first level, but the display unit displays the item of which information concealing level is a second level lower than the first level.

3. The portable medical information terminal according to claim 2, wherein in a case where the current position is a second position different from the first position, the display unit displays the item of which information concealing level is the first level and the item of which information concealing level is the second level.

4. The portable medical information terminal according to claim 1, wherein the at least one processor further functions to:
set each of the plurality of information concealing levels corresponding to each of the plurality of items included in the medical information stored in the at least one memory.

5. The medical information terminal according to claim 1, wherein the information concealing level indicates a degree that should not be known to a third party other than a doctor and a patient.

6. The medical information terminal according to claim 1, wherein the at least one processor obtains position information by a GPS (Global Positioning System).

7. The medical information terminal according to claim 1, wherein the at least one processor further functions to:
set the information concealing level for the plurality of items included in the medical information stored in the at least one memory,
wherein the setting includes allowing the information concealing level to be set for a part of the plurality of items, and if there are the information concealing levels for all the plurality of items, the setting includes comparing the information concealing level for all the plurality of items with the information concealing level for the part and includes determining the higher information concealing level as the information concealing level for the part of the plurality of items, and
wherein at a time that the display unit displays each of the plurality of items, the determined information concealing level is used for restricting displaying about the part of the plurality of items.

8. The medical information terminal according to claim 1, wherein the at least one processor further functions to:
authenticate a user,
wherein the information concealing level is raised if the user can be authenticated.

9. The medical information terminal according to claim 1, wherein the display unit does not display each of the plurality of items by executing processing of displaying by encryption, processing of applying ciphering or processing of non-display.

10. The medical information terminal according to claim 1, wherein the display unit does not display each of the plurality of items by enlarging the item which is not restricted in displaying about the medical information and displaying the enlarged item overlapping with the item with the information concealing level that is more than information concealing level of the item which is not displayed.

11. The medical information terminal according to claim 1, wherein the at least one processor further functions to:
set the information concealing level for the plurality of items included in the medical information stored in the at least one memory,
wherein the setting includes individually setting the information concealing level each for the patient regarding the medical information stored in the medical information terminal according to the obtained position information.

12. The medical information terminal according to claim 1, wherein the at least one processor obtains the position information of the medical information terminal by means of the LCS (Location Service) protocol defined in the LTE (Long Term Evolution) communication standard.

13. The medical information terminal according to claim 1, wherein the information concealing level is edited by an input of a user to the medical information terminal.

14. The medical information terminal according to claim 1, wherein the display unit does not display a part of the plurality of items by changing the part of the plurality of items into a content which is different from the part of the plurality of items.

15. The medical information terminal according to claim 1, wherein the display unit does not display a part of the plurality of items so that browsing of the part of the plurality of items is made difficult.

16. The medical information terminal according to claim 1, wherein the at least one processor further functions to:
set the information concealing level for a plurality of items included in the medical information stored in at least one memory, wherein the setting includes setting the information concealing level based on an item corresponding to the information concealing level from among the plurality of the items.

17. A control method of a portable medical information terminal capable of displaying medical information which is personal information of a patient, the portable medical information terminal comprising at least one memory storing (a) the medical information including a plurality of items, (b) a plurality of information concealing levels corresponding to each of the plurality of items included in the medical information, and (c) a program, the method comprising:
in a case where the medical information is browsed by a user, obtaining position information indicating a current position of the portable medical information terminal; and
determining whether a display unit displays each of the plurality of items included in the medical information by comparing a plurality of previously set position information corresponding to the plurality of information concealing levels of each of the plurality of items included in the medical information with the position information indicating the current position of the portable medical information terminal.

18. A portable medical information terminal capable of displaying medical information which is personal information of a patient comprising:
at least one memory storing (a) the medical information including a plurality of items and (b) a program; and
at least one processor which, by executing the program, functions to:
acquire first position information indicating a current position of the portable medical information terminal and second position information indicating a previously registered position; and conceal description contents of at least one of the plurality of items included in the medical information, in the case where the current position indicated by the first position information is not included in a range based on the second position information.

19. The portable medical information terminal according to claim 18, wherein the at least one processor is further configured to acquire an information concealing level in the plurality of items included in the medical information and conceal the description contents of at least one of the plurality of items included in the medical information based on the information concealing level, in the case where the current position indicated by the first position information is not included in a range based on the second position information.

20. The portable medical information terminal according to claim 18, wherein the at least one processor is further configured to display the description contents of at least one of the plurality of items without concealing the description contents based on a result of an authentication process.

21. The portable medical information terminal according to claim 18, wherein the at least one processor is further configured to conceal the description contents of at least one of the plurality of items included in the medical information based on the current positional information and types of the plurality of items.

22. The portable medical information terminal according to claim 18, wherein a conceal process includes at least one of a process of encrypting, a process of obfuscating, and a process of hiding.

* * * * *